United States Patent
Argembeaux et al.

(10) Patent No.: US 10,610,464 B2
(45) Date of Patent: Apr. 7, 2020

(54) COSMETIC PREPARATION COMPRISING PULVERIZED HYDROPHOBIC SUBSTANCES

(71) Applicant: BEIERSDORF AG, Hamburg (DE)

(72) Inventors: Horst Argembeaux, Wentorf (DE); Stefan Biel, Hamburg (DE); Katrin Counradi, Hamburg (DE); Ina Schornstein, Hamburg (DE); Svenja Lena Moellgaard, Hamburg (DE); Heike Miertsch, Hamburg (DE); Katja Maetzold, Hamburg (DE)

(73) Assignee: Beiersdorf AG, Hamburg (DE)

( * ) Notice: Subject to any disclaimer, the term of this patent is extended or adjusted under 35 U.S.C. 154(b) by 1089 days.

(21) Appl. No.: 14/355,616

(22) PCT Filed: Nov. 2, 2012

(86) PCT No.: PCT/EP2012/071682
§ 371 (c)(1),
(2) Date: May 1, 2014

(87) PCT Pub. No.: WO2013/064612
PCT Pub. Date: May 10, 2013

(65) Prior Publication Data
US 2014/0335188 A1    Nov. 13, 2014

(30) Foreign Application Priority Data

Nov. 3, 2011 (DE) .................. 10 2011 085 688

(51) Int. Cl.
| | |
|---|---|
| A61K 8/02 | (2006.01) |
| A61Q 15/00 | (2006.01) |
| A61Q 19/00 | (2006.01) |
| A61K 8/73 | (2006.01) |
| A61Q 17/04 | (2006.01) |

(52) U.S. Cl.
CPC .......... *A61K 8/0245* (2013.01); *A61K 8/0279* (2013.01); *A61K 8/73* (2013.01); *A61Q 15/00* (2013.01); *A61Q 17/04* (2013.01); *A61Q 19/00* (2013.01); *A61K 2800/10* (2013.01); *A61K 2800/20* (2013.01); *A61K 2800/56* (2013.01)

(58) Field of Classification Search
CPC ...... A61Q 15/00; A61Q 19/001; A61Q 90/00; A61Q 17/04; A61Q 19/08; A61K 8/022; A61K 8/25; A61K 8/73; A61K 8/731; A61K 8/027; A61K 2800/31; A61K 2800/49; A61K 8/0225; A61K 8/0245
See application file for complete search history.

(56) References Cited

U.S. PATENT DOCUMENTS

| | | | |
|---|---|---|---|
| 6,056,791 A | 5/2000 | Weidner et al. | |
| 6,440,336 B1 | 8/2002 | Weinreich et al. | |
| 7,303,767 B2 | 12/2007 | Withiam et al. | |
| 7,544,720 B2 | 6/2009 | Cooper et al. | |
| 8,242,182 B2 | 8/2012 | Cooper et al. | |
| 8,357,728 B2 | 1/2013 | Butler et al. | |
| 2006/0171973 A1 | 8/2006 | Withiam et al. | |
| 2007/0135528 A1 | 6/2007 | Butler et al. | |
| 2007/0298239 A1 | 12/2007 | Cooper et al. | |
| 2008/0044551 A1 | 2/2008 | Subramaniam | |
| 2008/0089856 A1* | 4/2008 | Kolly-Hernandez et al. ............... 424/70.122 | |
| 2008/0102275 A1 | 5/2008 | Calderone et al. | |
| 2008/0221231 A1 | 9/2008 | Cooper et al. | |
| 2010/0062029 A1 | 3/2010 | Roreger | |
| 2010/0183528 A1* | 7/2010 | Maloney .................. A61K 8/27 424/60 |
| 2010/0196484 A1 | 8/2010 | Aubrun et al. | |
| 2012/0189679 A1 | 7/2012 | Calderone et al. | |
| 2012/0258150 A1* | 10/2012 | Rauckhorst et al. ......... 424/401 |
| 2014/0056836 A1 | 2/2014 | Subramaniam | |

FOREIGN PATENT DOCUMENTS

| | | |
|---|---|---|
| CA | 2373513 A1 | 11/2000 |
| CA | 2312249 A1 | 12/2000 |
| CN | 103301028 A * | 9/2013 |
| DE | 19928851 A1 | 12/2000 |
| DE | 202004021155 U1 | 2/2007 |
| EP | 0744992 A1 | 12/1996 |
| EP | 0794760 A1 | 9/1997 |
| EP | 1021241 A1 | 7/2000 |
| EP | 1183003 A2 | 3/2002 |
| EP | 1908493 A1 | 4/2008 |
| WO | 9521688 A1 | 8/1995 |
| WO | 9617583 A1 | 6/1996 |
| WO | 9917868 A1 | 4/1999 |

(Continued)

OTHER PUBLICATIONS

M. Wehowski, E. Weidner, "Wasserhaltige Agglomerate durch Hochdruckspruehung nach dem CPF Verfahren", Chemie Ingenieur Technik 2005, 77, No. 3 pp. 274-278.

*Primary Examiner* — Robert S Cabral

(74) *Attorney, Agent, or Firm* — Abel Schillinger, LLP

(57) ABSTRACT

A substance, which is in principle insoluble in a cosmetic or dermatological preparation, is converted into a powdery product by absorption onto a carrier, wherein said powdery product can be distributed better in the preparation. The preparations comprise water and one or more hydrophobic substances or substance mixtures which are liquid and pasty at room temperature and/or meltable up to a temperature of 150° C. and which are absorbed on one or more particulate carriers. The hydrophobic substance or substance mixture in itself is insoluble or sparingly soluble in the preparation and the carriers are characterized by a particle size ranging from 5 nm to 2 mm, a tamped density of between 50 kg/m$^3$ and 1400 kg/m$^3$ and a spherical, fibrous, flocculated and/or sponge-like particulate form.

12 Claims, No Drawings

(56) References Cited

FOREIGN PATENT DOCUMENTS

| WO | 0067703 A2 | 11/2000 |
|---|---|---|
| WO | 2005014704 A1 | 2/2005 |
| WO | 2005073300 A1 | 8/2005 |
| WO | 2006082536 A1 | 8/2006 |
| WO | 2006083387 A1 | 8/2006 |
| WO | 2006097171 A1 | 9/2006 |
| WO | 2008041196 A1 | 4/2008 |

\* cited by examiner

COSMETIC PREPARATION COMPRISING PULVERIZED HYDROPHOBIC SUBSTANCES

BACKGROUND OF THE INVENTION

1. Field of the Invention

The invention encompasses cosmetic preparations comprising hydrophobic active ingredients or active solutions that are otherwise sparingly soluble in the preparation.

2. Discussion of Background Information

Cosmetic active ingredients or active solutions have to be present in homogeneously distributed form in a cosmetic formulation for good effectiveness. Substances of different polarity, however, cannot be stably combined with one another. This is achieved at best with the assistance of emulsifiers, the disadvantages of which, however, are not only the costs, but a relatively high irritation potential and a change (impairment) of the sensory properties. Furthermore, the release of active ingredients from the formulation can be hindered by emulsifiers.

Liquid substances are barely able to be stably combined with solid substance particles. These separate on account of the different densities. This problem can possibly be prevented by using gel formers or suspension auxiliaries which, besides higher costs, also lead to an impairment of the sensory properties and to defective distributability.

Furthermore, liquid substances cannot be combined with solid substance particles which are soluble in the liquid substance. However, their solid properties are often desired, as the example of sugar crystals in water shows.

Although hydrophilic active ingredients can be incorporated very readily in monophase hydrophilic systems, e.g. aqueous solutions, lipophilic raw materials, such as oils and perfumes can only be used in undissolved form e.g. as wax beads or in dissolved form e.g. through the use of solubilizers. In emulsions, emulsifiers are necessary in order to homogeneously stably mix hydrophilic and lipophilic phase with one another.

Various methods of the pulverization of substances that are liquid or meltable at room temperature are known in the prior art.

WO 9617583 A1 describes humectants absorbed on silica carriers.

WO 2005 073300 A1 describes an improvement in the solubility of primary alkyl sulfates (PAS) in detergents for use at low temperatures. The production of the porous bodies takes place by separation of freeze-dried emulsions into disperse and continuous phases. In this, liquid is not applied to a carrier particle, but rather liquid is removed by freeze drying so that hollow cavities are formed.

WO 2006 082536 A1 describes spray-dried preparations of active ingredients which are present in a carrier made of gum arabic mixed with a surfactant. The technology serves for the encapsulation of menthol for chewing gums and tablets.

WO 2008 041196 A1 describes a pulverized, non-liquid hair conditioning product, where the liquid conditioner is absorbed on a solid carrier. The powdery product is mixed with water prior to use.

EP 1 183 003 A1 describes the so-called spray-drying, WO 2005 073300 A1 describes freeze-drying, WO 2005 014704 A1 describes CO2 drying and WO 95 21688 A1 describes the so-called PGSS process. It is a disadvantage of the last-mentioned process that the resulting pulverized liquid has to be further cooled afterwards if its melting temperature is below the ambient temperature.

WO 99 17868 A1, EP 1 021 241 A1 and EP 0 744 992 A1 describe the so-called CPF (concentrated powder form) process. In the CPF process, liquids or liquid mixtures are converted to powder form by supercritical carbon dioxide (CO2) without loss of valuable substances. The CO2-gas-containing liquids are decompressed rapidly via a nozzle. This produces a very fine droplet spray at temperatures of −10° C. to +10° C. In parallel, a powdery carrier is metered into the droplet spray. The addition of carrier is the difference compared to the PGSS process. This carrier binds the fine droplets and produces a free-flowing powder. The resulting powder can have a liquid fraction of up to at most 99% by weight, based on the total mass of the powder.

CPF technology can be used to produce pourable powders with a high liquid fraction. Besides CO2, any gas can in principle be used in which the liquid to be powdered dissolves.

The higher the melting temperature of the liquid, the less carrier material is required for stabilizing the pulverized liquid. The fraction of the carrier can therefore preferably be between 1 and 90% by weight.

Carriers or auxiliaries that can be used are any solid, powdery substance, although it is advantageous if its particle size is less than 100 μm or if one of the carriers has a porosity, such as, for example, activated carbon or zeolites.

The advantages of the CPF process are that degradation reactions are slowed or prevented by the low temperatures during the pulverization; only slight odor nuisances result and the inert CO2 acts as protective gas for reactive substances.

The CPF process is already used in food technology, detergent technology, paint, coatings and adhesive technology.

WO 2008 041196 A1 describes this CPF process for providing a pulverized, non-liquid hair conditioner product.

DE 202004021155 U1 describes preparations in which at least 10% by weight of a substance to be adsorbed consisting of at least active ingredient (A) and stabilizer (B) are present in the internal pore volume of a carrier (C).

If the component to be adsorbed (A) is an oil-soluble compound, then polysaccharides, chelators, glycerides or emulsifiers are used as stabilizers (B). Low molecular weight inorganic or organic compounds, as well as higher molecular weight organic compounds of natural or synthetic origin are named as carriers (C).

Carriers (C) are optionally also polysaccharides, in which case polysaccharides different from C) are then used as stabilizers B).

It is desirable to also stably incorporate hydrophobic substances or substance mixtures, such as e.g. active ingredients, into water-containing or hydrophilic formulations without using emulsifiers or stabilizers. The efficacy of the active ingredients can be reduced if they are in undissolved form in the formulation, consequently also arrive at the skin in undissolved form and only then have to be dissolved on the skin. The skin sebum present or perspiration is inadequate here as solvent. The aim is therefore the use of active ingredients which are predissolved in hydrophobic solvent. These dissolved substances cannot be incorporated directly into water-containing formulations. The use of emulsifiers in order to emulsify hydrophobic fractions in a lipophobic environment leads inter alia to a hindering of the release of the active ingredients.

SUMMARY OF THE INVENTION

The invention is therefore a cosmetic or dermatological preparation comprising water and one or more powdery products, comprising or consisting of one or more hydrophobic substances or substance mixtures that are liquid or pasty at room temperature and/or meltable up to a temperature of 150° C. (a.), which are absorbed on one or more particulate carriers (b.). The substance or substance mixture (a.) is by itself insoluble or sparingly soluble in the preparation. The substance or substance mixture is considered to be soluble if it is present in completely and homogeneously dissolved form in the surrounding medium, i.e. the preparation, without further auxiliaries such as emulsifiers or solubilizers. By itself means here that the substance is not absorbed on the carrier.

The carriers (b.) are characterized by an average particle size in the range from 5 nm to 2 mm, a tamped density of from 50 kg/m$^3$ to 1400 kg/m$^3$ and a spherical, fibrous, flocculated and/or sponge-like particulate form. The carriers used are powders which have minimum 5 nm and maximum 2 mm in the average particle size.

A particularly decisive factor for selecting the carrier material is its tamped density. The tamped density is 50 kg/m$^3$ to 1400 kg/m$^3$. The tamped density is ascertained by determining the volume, the tamped volume being the smallest volume of a released amount of filler material which is present after tamping or compacting according to standardized conditions (see also ISO 787/11). The porosity of the carrier can be freely selected from nonporous to highly porous.

The particulate form of the carrier is spherical, fibrous, flocculated or sponge-like.

DETAILED DESCRIPTION OF THE INVENTION

The carrier substances are powder substances customarily used in cosmetics. They are preferably selected from the group of polysaccharides and silicas and derivatives thereof; powder substances as are used in decorative cosmetics as filler and sensory additive are also possible. The list below of carrier materials that can be used advantageously should in no way be limiting:

Polysaccharides:
  starches from different plant sources, e.g. corn starch, potato starch, rice starch, wheat starch, and derivatives thereof (e.g. trade names: Amylogum CLS from Avebe, C*EmCap from Cerestar, DryFlo grades from Akzo Nobel
  celluloses and derivatives, e.g. Avicel grades from FMC Biopolymer, Arbocel, Vitacel, Vivapur grades from J. Rettenmaier & Söhne GmbH.

Further fillers such as lauroyl lysine (Amihope LL), nylon grades (e.g. Orgasol grades from Arkema) or silicates such as calcium silicate (Hubersorb from Huber) can be used. In the case of the silicas, preferably grades from the series of Aerosils from Evonik Degussa can be used.

The powdery products include the hydrophobic substances or substance mixtures (a.) and the particulate carriers (b.) on which they are absorbed, or preferably they consist only of these two constituents a.) and b.).

It is possible to dispense with the addition of emulsifiers or stabilizers in the powdery products.

A further preferred criterion is that the powdery products are produced according to the CPF process.

According to the invention, the hydrophobic substance or the substance mixture is characterized in that, by itself, it is insoluble or sparingly soluble in the preparation. Here, a hydrophobic substance or a hydrophobic substance mixture is characterized in that it is immiscible with water. Solubility is the property of a substance to dissolve homogeneously in a liquid or melt.

As a result of pulverizing the hydrophilic substances or substance mixtures, also referred to as active ingredients or active solutions, it is now possible according to the invention to incorporate these without further auxiliaries such as solubility promoters or emulsifiers into formulations in which they are not soluble in a homogeneous manner, i.e. without phase separation.

I.e. a substance that is in principle insoluble in a cosmetic or dermatological preparation is converted to a powdery product as a result of absorption on a carrier and homogeneously distributed in the preparation, where the substance insoluble in the hydrophilic formulation is bonded as hydrophobic solution to the carrier. The powder laden with active ingredients does not dissolve here in the preparation, but is present in the formulation such as a sensory additive as powder, only additionally laden with liquid.

Pulverization advantageously takes place according to the CPF process. Reference is hereby expressly made to the CPF processes described in documents WO 99 17868 A1, EP 1 021 241 A1 and EP 0 744 992 A1. The disclosures made therein are in their entirety also part of the present application.

The CPF process makes it possible to produce powdery solids from liquids. The process principle consists in dissolving a gas in the liquid to be pulverized under elevated pressure, preferably until a gas-saturated solution is obtained. Compared to pure liquid, such a solution has a series of favorable properties:

Thus, normally, the viscosity of this solution is lowered by several orders of magnitude compared to the pure liquid at the same temperature, and the interfacial tension is also considerably reduced.

The pressurized liquid/gas solution is then fed to a decompression element and rapidly decompressed therein. Before the decompression element, in the decompression element or after it, in particular shortly after the decompression element, a solid, powdery auxiliary, the particulate carrier, is admixed with the liquid substance or substance mixture to be pulverized or the liquid/gas solution.

The gas used can in principle be any gas which is sufficiently soluble in the liquid substance or substance mixture to be pulverized. For example, the gas that can be used is carbon dioxide, a hydrocarbon, in particular methane, ethane, propane, butane, ethene, propene or a halogenated hydrocarbon, an ether, an inert gas, in particular nitrogen, helium or argon, a gaseous oxide, in particular dinitrogen oxide or sulfur dioxide, and ammonia. A mixture of two or more of the aforementioned gases can also be used. The increased pressure under which the gas is dissolved in the liquid substance or substance mixture can be in the range from 5 bar to 800 bar, although preferably the pressure is in the range from 10 bar to 350 bar and particularly preferably in the range from 20 bar to 250 bar.

Preferably, the dissolution of the gas in the liquid substance or substance mixture is accelerated by mixing the gas with the liquid substance or substance mixture. This mixing can be achieved for example by shaking or rolling the pressurized container in which the liquid to be pulverized has been introduced. Alternatively, the solution that is formed in the pressurized container can be stirred using a stirrer. Another option of achieving thorough mixing of the liquid to be pulverized with the gas consists in recirculating the liquid phase present in the pressurized container and/or the gas phase, i.e. pumping it/them from the pressurized container and introducing it/them again to the pressurized container in the region of the respective other phase. A further option is the use of a static mixer. The aforementioned procedures can of course also be combined.

The CPF process functions in principle with any solid, powdery carrier.

The substance to be pulverized, the active solution, is bound here to the carrier particle by adhesion, impregnation and/or agglomeration. Surprisingly, the CPF process does not lead to a closed envelope being formed. Capsules are not formed. Consequently, the hydrophobic active solution can detach from the particulate carrier as soon as the laden particles come into an environment in which the active solution is soluble and/or to which there exists an affinity. Thus, for example, the hydrophobic substances can bind with the skin sebum on the skin and thus attach to the skin. The release then takes place also with a time delay and thus leads to a long-lasting effect.

On account of the special production technology with CPF technology, the substance, active ingredient on the particles is already present in predissolved form at the site of action and can be very rapidly released. The thus improved solubility is comparable with that of instant coffee compared to coffee powder.

According to the invention, hydrophobic substance, substance mixture, active ingredient or active solution to be pulverized are to be understood as meaning all substances that are liquid or pasty at room temperature and/or meltable up to a temperature of 150° C.

The active solution is preferably liquid at room temperature, but can also be pasty to solid if it is then meltable at a temperature up to 150° C.

Preferred cosmetic active ingredients which can be present in the preparation and are preferably pulverized by means of CPF are to be selected from the group of antibacterial, antiperspirant, anti-aging, skin-calming and/or moisturizing active ingredients.

Deodorant active ingredients such as farnesol, dimethyl phenyl butanol or other active ingredients, such as ubiquinone, thymol or oryzanol, can likewise be selected. Furthermore, oil-soluble UV filters can be used, e.g. Butyl Methoxydibenzoylmethane or Bis-Ethylhexyloxyphenol Methoxyphenyl Triazine.

Further active ingredients can be selected from the group of extracts, such as e.g. of/from *Persea Gratissima, Fucus Vesiculosas, Hamamelis Virginiana, Chamomilla Recutita* flower extract, cotton seed oil, *Simmondsia Chinensis* (jojoba) oil, menthol, *Glycyrrhiza Glabra.*

According to the invention, now hydrophobic deodorant actives can for example be incorporated into water-containing formulations.

The substances, active ingredients or active solutions to be incorporated are insoluble or only sparingly soluble in the preparation. The solubility is the property of a substance to dissolve homogeneously in a liquid. Substance or substance mixtures which cannot dissolve completely in the solvent or can only dissolve inhomogeneously in solvents are referred to as insoluble or sparingly soluble, respectively.

The cosmetic and dermatological preparations according to the invention can also comprise cosmetic auxiliaries and further active ingredients, as are customarily used in such preparations, e.g. preservatives, preservation aids, bactericides, perfumes, substances for preventing foaming, dyes and colored pigments, thickeners, moisturizing and/or humectant substances, fats, oils, waxes or other customary constituents of a cosmetic or dermatological formulation, such as alcohols, polyols, polymers, foam stabilizers, electrolytes, organic solvents or silicone derivatives, provided the addition does not adversely affect the required properties as regards solubility.

What is claimed is:

1. A cosmetic or dermatological preparation, wherein the preparation is present in the form of a packaged product which comprises water and, incorporated therein, one or more powdery materials comprising or consisting of (i) one or more hydrophobic substances or substance mixtures which comprise one or more of ubiquinone, thymol, and oryzanol, are liquid or pasty at room temperature and/or meltable up to a temperature of 150° C. and on their own are insoluble or sparingly soluble in a remainder of the preparation, bound by at least one of adhesion, impregnation, agglomeration to (ii) one or more particulate carriers having an average particle size in a range of from 5 nm to 2 mm and a tamped density of from 50 kg/m$^3$ to 1400 kg/m$^3$, and being of a spherical, fibrous, flocculated and/or sponge-like form.

2. A cosmetic or dermatological preparation, wherein the preparation is present in the form of a packaged product which comprises water and, incorporated therein, one or more powdery materials comprising or consisting of (i) one or more hydrophobic substances or substance mixtures which comprise at least one of farnesol and dimethyl phenyl butanol, are liquid or pasty at room temperature and/or meltable up to a temperature of 150° C. and on their own are insoluble or sparingly soluble in a remainder of the preparation, bound by at least one of adhesion, impregnation, agglomeration to (ii) one or more particulate carriers having an average particle size in a range of from 5 nm to 2 mm and a tamped density of from 50 kg/m$^3$ to 1400 kg/m$^3$, and being of a spherical, fibrous, flocculated and/or sponge-like form.

3. A cosmetic or dermatological preparation, wherein the preparation is present in the form of a packaged product which comprises water and, incorporated therein, one or more powdery materials comprising or consisting of (i) one or more hydrophobic substances or substance mixtures which comprise at least one oil-soluble UV filter, are liquid or pasty at room temperature and/or meltable up to a temperature of 150° C. and on their own are insoluble or sparingly soluble in a remainder of the preparation, bound by at least one of adhesion, impregnation, agglomeration to (ii) one or more particulate carriers having an average particle size in a range of from 5 nm to 2 mm and a tamped density of from 50 kg/m$^3$ to 1400 kg/m$^3$, and being of a spherical, fibrous, flocculated and/or sponge-like form.

4. The preparation of claim 3, wherein the at least one oil-soluble UV filter comprises at least one of butyl methoxydibenzoylmethane and bis-ethylhexyloxyphenol methoxyphenyl triazine.

5. The preparation of claim 3, wherein (i) has been bound to (ii) by a Concentrated Powder Form (CPF) process.

6. The preparation of claim 3, wherein (ii) comprises a polysaccharide.

7. The preparation of claim 6, wherein (ii) comprises cellulose and/or a cellulose derivative.

8. The preparation of claim 6, wherein (ii) comprises a starch.

9. The preparation of claim 3, wherein (ii) comprises one or more of silica and a silicate.

10. The preparation of claim 3, wherein (ii) comprises one or more of a nylon and lauroyl lysine.

11. The preparation of claim 3, wherein the one or more powdery materials consist of (i) and (ii).

12. The preparation of claim 3, wherein the one or more powdery materials are free of emulsifiers and stabilizers.

\* \* \* \* \*